United States Patent [19]

Stack

[11] Patent Number: 4,788,290

[45] Date of Patent: Nov. 29, 1988

[54] SEROTONERGIC PYRAZINE DERIVATIVES

[75] Inventor: Gary P. Stack, Merion, Pa.

[73] Assignee: American Home Products Corporation, New York, N.Y.

[21] Appl. No.: 131,868

[22] Filed: Dec. 11, 1987

[51] Int. Cl.[4] .................. C07D 405/14; C07D 407/14; C07D 409/14; C07D 411/14

[52] U.S. Cl. .................... 544/357; 544/336; 544/377

[58] Field of Search ............... 544/357, 105

[56] References Cited

U.S. PATENT DOCUMENTS

| 3,058,980 | 10/1962 | Berg | 544/105 |
|---|---|---|---|
| 3,470,185 | 9/1969 | Huebner et al. | 544/376 |
| 3,917,597 | 11/1975 | Regnier et al. | 544/357 |
| 3,944,549 | 3/1976 | Lafon | 544/377 |
| 4,163,849 | 8/1979 | Lumma, Jr. et al. | 544/357 |
| 4,704,390 | 11/1987 | Caprathe et al. | 544/357 |

FOREIGN PATENT DOCUMENTS 1492528 4/1976 United Kingdom .

Primary Examiner—Glennon H. Hollrah
Assistant Examiner—James H. Turnipseed
Attorney, Agent, or Firm—Richard K. Jackson

[57] ABSTRACT

The compounds

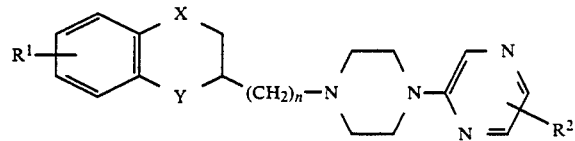

in which
X and Y are, independently, —O— or —S—;
R[1] and R[2] are, independently, halo, trifluoromethyl, cyano, hydroxy, amino, alkylamino, dialkylamino, alkoxy, alkyl or alkanoylamino; and
n is 1 to 4;

or a pharmaceutically acceptable salt thereof, are selective serotonergic agents useful in the treatment of depression and/or anxiety, as well as related sexual dysfunctions and appetite disorders.

5 Claims, No Drawings

SEROTONERGIC PYRAZINE DERIVATIVES

DESCRIPTION OF THE INVENTION

In accordance with this invention, there is provided a group of compounds of the formula:

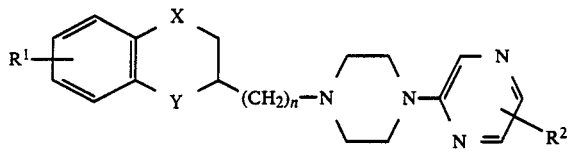

in which

X and Y are, independently, —O— or —S—;

$R^1$ and $R^2$ are, independently, hydrogen, halo, trifluoromethyl, cyano, hydroxy, amino, alkylamino of 1 to 6 carbon atoms, dialkylamino of 2 to 12 carbon atoms, alkoxy of 1 to 6 carbon atoms, alkyl of 1 to 6 carbon atoms or alkanoylamido 2 to 6 carbon atoms;

n is one of the integers 1, 2, 3 or 4;

or a pharmaceutically acceptable salt thereof. Of these compounds, the preferred members are those in which X and Y are both oxygen. The halogens embraced by the term halo are chlorine, bromine, iodine and fluorine, preferably chlorine, bromine or fluorine.

The compounds of the invention are prepared by conventional methods. For example, a suitably substituted piperazine is reacted with the appropriate pyrazinylhalide under the influence of a base such as diisopropylethylamine in a solvent such as dimethylformamide.

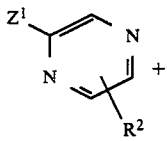

Conversely, the piperazine, already substituted with the desired pyrazine, may be caused to react with the appropriate alkylating agent (where $Z^2$ is chlorine, bromine, tosyloxy, and the like) with or without base present to provide the compounds of the genus described above.

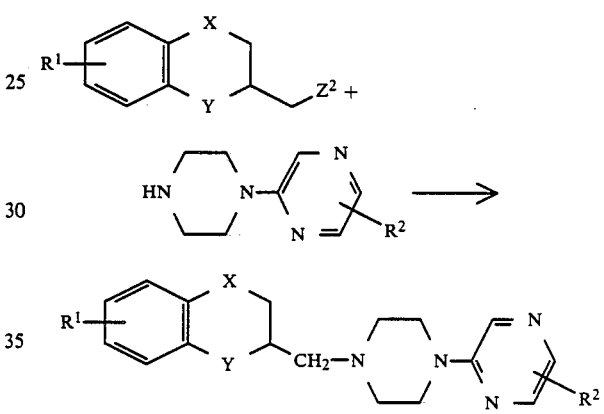

Alternatively, the piperazine may actually be formed in the final reaction through the interaction of the desired bis-(2-haloethyl)aminopyrazine with the appropriately substituted primary amine in the presence of base.

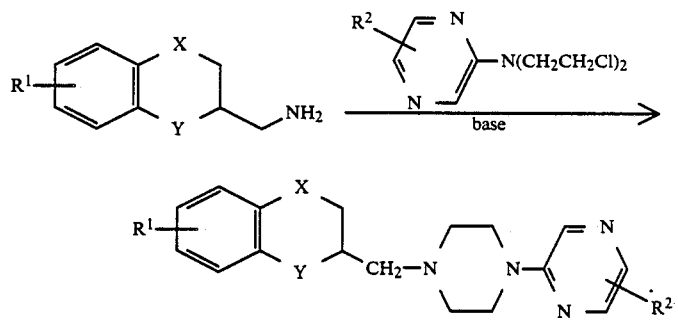

In addition, the appropriate acid halide may be combined with the desired pyrazinylpiperazine and the resulting amide reduced to the amine with a suitable reducing agent such as lithium aluminum hydride or borane tetrahydrofuran complex ($BH_3$.THF).

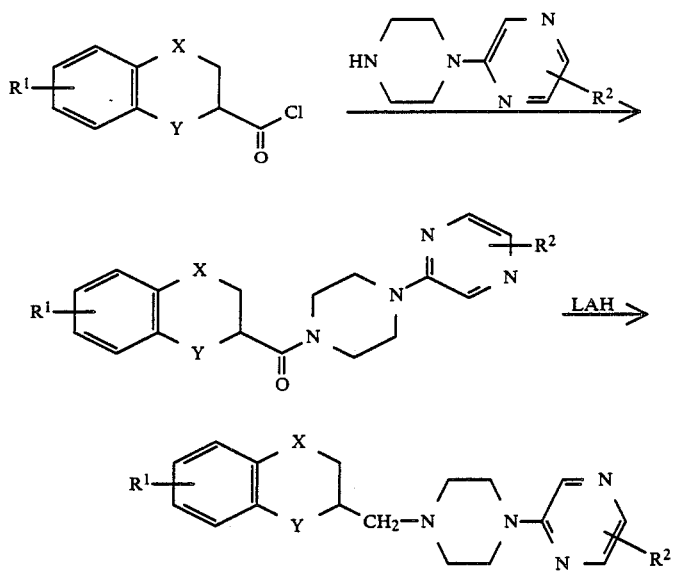

The pharmaceutically acceptable salts of the compounds of this invention are derived by conventional means from such acids as hydrochloric, hydrobromic, sulfuric, phosphoric, nitric, methanesulfonic, p-toluenesulfonic, acetic, citric, maleic, succinic acid and the like.

The following examples illustrate, without limitation, the preparation of representative compounds of the invention.

EXAMPLE 1

2-Chloro-6-[4-(2,3-dihydro-1,4-benzodioxin-2-ylmethyl)-1-piperazinyl]pyrazine 1-(2,3-Dihydro-1,4-benzodioxin-2-ylmethyl)piperazine (4.7 g, 20 mmole) and 2,6-dichloropyrazine (3.0 g, 20 mmole) were combined in 200 ml of dimethylformamide and 2.6 g (20 mmole) of diisopropylethylamine was added. The mixture was heated under nitrogen at 60° C. for 24 hours. The solvent was then removed in vacuum and the residue filtered through 75 g of silica gel with chloroform as the eluent. The product-containing fractions were concentrated in vacuum and the residue was crystallized from methanol with addition of 4N isopropanolic HCl and recrystallized from methanol to give 4.26 g of the title compound as the monohydrochloride, m.p. 270°–280° C.

Elemental analysis for $C_{17}H_{19}N_4O_2Cl\cdot HCl$; Calc'd: C, 53.27; H, 5.26; N, 14.62; Found: C, 53.05; H, 5.15; N, 14.40.

EXAMPLE 2

2-Chloro-3-[4-(2,3-dihydro-1,4-benzodioxin-2-ylmethyl)-1-piperazinyl]pyrazine 1-(2,3-Dihydro-1,4-benzodioxin-2-ylmethyl)piperazine (2.35 g, 10 mmole), 2,3-dichloropyrazine (1.5 g, 10 mmole) and diisopropylethylamine (1.3 g, 10 mmole) were combined in 100 ml of dimethylformamide and heated at 75° C. under $N_2$ for 24 hours. The solvent was removed in vacuum and the residue was filtered through 75 g of silica gel using choroform as the eluent. The relevant fractions were combined, the solvent evaporated and the residue crystallized from isopropanol with addition of 4N isopropanolic HCl to give 2.1 g of title compound as the hydrochloride, m.p. 217°–218° C.

Elemental Analysis for $C_{17}H_{19}N_4O_2Cl\cdot HCl$; Calc'd: C, 53.27; H, 5.26; N, 14.62; Found: C, 53.18; H, 5.34; N, 14.28.

EXAMPLE 3

2-[4-(2,3-Dihydro-1,4-benzodioxin-2-ylmethyl)-1-piperazinyl]pyrazine 1-(2,3-Dihydro-1,4-benzodioxin-2-ylmethyl)piperazine (2.35 g, 10 mmole), 2-chloropyrazine (1.15 g, 10 mmole) and diisopropylethylamine (1.3 g, 10 mmole) were combined in 100 ml of 1-methyl-2-pyrrolidinone and heated under $N_2$ at 100° C. for 24 hours. Upon cooling, the solvent was removed in vacuum and the residue filtered through 75 g of silica gel using chloroform as the eluent. The product-containing fractions were combined, the solvent evaporated and the residue was crystallized from methanol with addition of 4N isopropanolic HCl. A second recrystallization from methanol gave 850 mg of title compound, as the dihydrochloride salt, m.p. 248°–253° C.(d).

Elemental analysis for $C_{17}H_{20}N_4O_2\cdot HCl$; Calc'd: C, 53.00; H, 5.75; N, 14.54; Found: C, 53.35; H, 5.74; N, 14.47.

The serotonergic properties of the compounds of this invention were established by the procedure of Hall et al., J. Neurochem. 44 1685 (1985) by demonstrating that the above-exemplified compounds displace $^3H$-8-OH-DPAT (dipropylaminotetralin) from the 5-$HT_{1A}$ serotonin receptor subtype. The results of this standard pharmacological procedure are reported in the following Table in conjunction with their dopaminergic activity which was determined in accordance with a modification of the procedure of Fields et al., Brain Res. 136 578 (1977) and Yamamura et al. eds., Neurotransmitter Receptor Binding, Raven Press, N.Y. (1978), wherein homogenized limbic brain tissue is incubated with $^3H$-spiroperidol at 1 $\mu M$ concentration of test compound to determine the binding inhibition afforded by the test compound.

TABLE

| Example | Inhibition of [³H] 8-OH DPAT at 1 μM conc. test compound | Inhibition of [³H] spiroperidol at 1 μM conc. test compound |
| --- | --- | --- |
| 1. | 94% | 0% |
| 2. | 48% | — |
| 3. | 85% | 52% |

The results of these experiments demonstrate, especially for the products of Examples 1 and 3, excellent affinity for the 5-HT$_{1A}$ serotonin receptor, and especially in the case of the product of Example 1 little or no binding at the D$_2$ dopamine receptor. This pharmacological profile resembles that of the known anxiolytics buspirone, gepirone and ipsapirone and the antidepressant 8-OH DPAT, which also show selective 5-HT$_{1A}$ serotonin affinity.

Based upon the similar pharmacological profile of the compounds of this invention and the known anxiolytics and antidepressants referred to above, the compounds of this invention are characterized as anxiolytic/antidepressant agents useful in the treatment of depression and in alleviating anxiety which conditions are directly manifested or indirectly involved in problems such as sexual dysfunction, senile dementia, eating disorders, and the like. The weak binding potential for the D$_2$ dopamine receptor further categorizes the compounds of this invention as possessing a very low liability for extra-pyramidal side effects which are known to attend dopamine binding activity.

Hence, the compounds of this invention are anxiolytic-antidepressant agents which may be administered to a patient in need thereof, either neat or with a conventional pharmaceutical carrier. The pharmaceutical carrier may be solid or liquid as suitable for oral or parenteral administration.

A solid carrier can include one or more substances which may also act as flavoring agents, lubricants, solubilisers, suspending agents, fillers, glidants, compression aids, binders or tablet-disintegrating agents; it can also be an encapsulating material. In powders, the carrier is a finely divided solid which is in admixture with the finely divided active ingredients. In tablets, the active ingredient is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose), alcohols (including monohydric alcohols and polyhydric alcohols, e.g., glycols) and their derivatives, and oils (e.g. fractionated coconut oil and arachis oil).

For parenteral administration, the carrier can also be an oil ester such as ethyl oleate and isopropyl myristate. Sterile liquid carriers are used in sterile liquid form compositions for parenteral administration. The liquid carrier for pressurized compositions can be a halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. When the compound is orally active, it can be administered orally either in liquid or solid composition form.

Preferably, the pharmaceutical composition is in unit dosage form, e.g. as tablets or capsules. In such form, the composition is subdivided in unit dose containing appropriate quantities of the active ingredients; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of anxiety or depression must be subjectively determined by the attending physican. The variables involved include the specific state of depression or anxiety and the size, age and response pattern of the patient.

What is claimed is:

1. A compound of the formula:

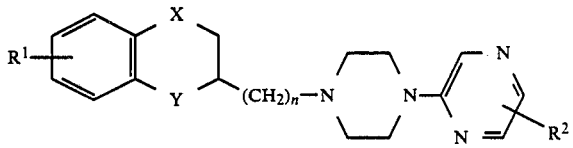

in which

X and Y are, independently, —O— or —S—;

R$^1$ and R$^2$ are, independently, hydrogen, halo, trifluoromethyl, cyano, hydroxy, amino, alkylamino of 1 to 6 carbon atoms, dialkylamino of 2 to 12 carbon atoms, alkoxy of 1 to 6 carbon atoms, alkyl of 1 to 6 carbon atoms or alkanoylamido of 2 to 6 carbon atoms; and n is one of the integers 1, 2, 3 or 4;

or a pharmaceutically acceptable salt thereof.

2. A compound of claim 1 of the formula:

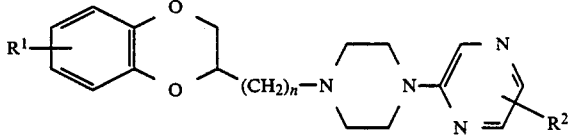

in which

R$^1$ and R$^2$ are, independently, hydrogen, halo, trifluoromethyl, cyano, hydroxy, amino, alkylamino of 1 to 6 carbon atoms, dialkylamino of 2 to 12 carbon atoms, alkoxy of 1 to 6 carbon atoms, alkyl of 1 to 6 carbon atoms or alkanoylamido of 2 to 6 carbon atoms; and n is one of the integers 1, 2, 3 or 4;

or a pharmaceutically acceptable salt thereof.

3. The compound of claim 1 which is 2-(4-(2,3-dihydro-1,4-benzodioxin-2-ylmethyl)-1-piperazinyl]pyrazine or a pharmaceutically acceptable salt thereof.

4. The compound of claim 1 which is 2-chloro-6-[4-(2,3-dihydro-1,4-benzodioxin-2-ylmethyl)-1-piperazinyl]pyrazine or a pharmaceutically acceptable salt thereof.

5. The compound of claim 1 which is 2-chloro-3-[4-(2,3-dihydro-1,4-benzodioxin-2-ylmethyl)-1-piperazinyl]pyrazine or a pharmaceutically acceptable salt thereof.

* * * * *